(12) United States Patent
Mandava

(10) Patent No.: US 10,351,504 B1
(45) Date of Patent: Jul. 16, 2019

(54) SYNTHESIS OF HYDROXYFLUORENE-CARBOXILIC ACID AND ESTERS THEREOF

(71) Applicant: Naga Bhushan Mandava, Potoma, MD (US)

(72) Inventor: Naga Bhushan Mandava, Potoma, MD (US)

( * ) Notice: Subject to any disclaimer, the term of this patent is extended or adjusted under 35 U.S.C. 154(b) by 0 days.

(21) Appl. No.: 16/126,386

(22) Filed: Sep. 10, 2018

Related U.S. Application Data

(60) Provisional application No. 62/557,191, filed on Sep. 12, 2017.

(51) Int. Cl.
| | | |
|---|---|---|
| *C07C 46/00* | (2006.01) | |
| *C07C 51/00* | (2006.01) | |
| *C07C 67/00* | (2006.01) | |
| *C07C 46/04* | (2006.01) | |
| *C07C 67/08* | (2006.01) | |
| *C07C 62/32* | (2006.01) | |
| *C07C 69/757* | (2006.01) | |
| *C07C 46/10* | (2006.01) | |
| *C07C 50/16* | (2006.01) | |

(52) U.S. Cl.
CPC .............. *C07C 46/04* (2013.01); *C07C 51/00* (2013.01); *C07C 67/08* (2013.01); *C07C 46/10* (2013.01); *C07C 50/16* (2013.01); *C07C 62/32* (2013.01); *C07C 69/757* (2013.01); *C07C 2603/18* (2017.05)

(58) Field of Classification Search
CPC ......... C07C 46/04; C07C 51/00; C07C 67/08; C07C 50/16
See application file for complete search history.

(56) References Cited

U.S. PATENT DOCUMENTS 4,510,090 A    4/1985   Tonnius
7,589,230 B2   9/2009   Tiwari

*Primary Examiner* — Sikarl A Witherspoon
(74) *Attorney, Agent, or Firm* — Steve O'Donnell

(57) ABSTRACT

Methods of synthesizing phenanthrenequinone, 9-hydroxyfluorene-9-5 carboxylic acid ("HFCA"), methyl-9-hydroxyfluorene-carboxylate ("HFCA methyl ester") and methyl-2-chloro-9-hydroxyfluorenecarboxylate, ("Chlorflurenol") starting from preferred embodiment are disclosed. Several reaction products of phenanthrene are useful in industry, and are valuable plant growth regulators.

5 Claims, 2 Drawing Sheets

SYNTHESIS OF HYDROXYFLUORENE-CARBOXILIC ACID AND ESTERS THEREOF

FIELD OF THE INVENTION

The subject matter of this application concerns organic chemical synthesis broadly and more particularly methods of synthesizing phenanthrenequinone from phenanthrene. The subject matter of this application further pertains to methods for synthesizing 9-hydroxyfluorene-9-carboxylic acid ("HFCA"), and esters thereof including methyl-9-hydroxyfluorene-carboxylate ("HFCA methyl ester") and methyl-2-chloro-9-hydroxyfluorenecarboxylate, ("Chlorflurenol").

BACKGROUND

Phenanthrenequinone may be used to produce several chemicals with wide ranging applications. Phenanthrenequinone can be used to synthesize fluorene, which in turn can be used to derive compounds that are being developed and investigated as wake-promoting agents similar to modafinil, and one derivative of fluorene, 9-hydroxyfluorene, is being researched for its medical potential in treating psoriasis and alopecia areata. Other derivatives of fluorine are used to prepare certain dyes such as Victoria Blue, for thermal and light sensitizers, in liquid crystal chemistry and illuminescence chemistry, spectrophotometric analysis and in the formation of organometallic complexes.

Further, derivatives of phenanthrenequinone have uses in electronics and in pharmaceutical as potential antihistamines or antispasmodics, or to increase bioavailability and retention time of some drugs.

Other derivatives of phenanthrenequinone are HFCA and its esters known as "morphactins" because they induce morphological changes in plants. the morphactins regulate plant growth activity by inhibiting auxin transport. Auxin regulates several plant growth processes and treatment with morphactins inhibit seed germination, stem elongation, and the growth and formation of shoot organs. The simplest morphactin is the pesticide HFCA n-butyl ester. It is synthesized similarly to HFCA-methyl ester, but the esterification of n-butanol ester is used in place of methanol. Subsequent chlorination of methyl ester yields monochloro and dichloro esters of HFCA, both of which are called chlorflurenol-methyl ester (CFM), or just chlorflurenol for short. Chlorflurenol is a registered pesticide in the US.

HFCA can be used to synthesize the plant growth regulator HFCA-methyl ester, which in turn, can be used to synthesize yet other plant growth regulators. Chlorflurenol exhibits some unique qualities in growth inhibition and demonstrates herbicidal activity by controlling broadleaf weeds as well as resistant weeds in turf and ornamentals. CHF is also useful for propagating the sucker population of pineapple plants and can increase their typical production rate of 0-3 per plant up to 35 per plant when chlorflurenol is applied at 1 lb. per acre. Chlorflurenol has also been found to control seedhead suppression in both warm and cool season turf grasses. (Unpublished study).

A critical step in the synthesis of many chemical species described above is the synthesis of phenanthrenequinone from phenanthrene.

SUMMARY

The subject matter of this application pertains to methods for synthesizing phenanthrenequinone and esters thereof. More particularly, the subject matter of this application pertains to methods for synthesizing phenanthrenequinone by oxidation of the phenanthrene followed by alkaline hydrolysis to yield HFCA which can be further covered to a corresponding methyl ester by esterification with ethanol.

BRIEF DESCRIPTION OF THE ILLUSTRATIONS

DETAILED DESCRIPTION

The synthesis of phenanthrenequinone begins by using chromic acid to oxidize phenanthrene via the Benzil-Benzilic Acid Rearrangement of alphadiketones. During the reaction the oxygen of the carbonyl group that is attacked by the —OH group is first coordinated to the sodium of potassium ion of NaOH of KOH. The yield of phenanthrenequinone can be increased with certain catalysts. For example, in U.S. Pat. No. 4,510,090 the reaction is done by lowering the temperature of the reaction and then slowly adding sulfuric acid. The sulfuric acid produces a steady source of the oxidizing age chromic acid from sodium dichromate.

HFCA is produced when phenanthrenequinone is reacted with NaOH. A hydroxyl group acting as a nucleophile attacks one of the acetyl-carbons or phenanthrenequinone, breaking the six carbon ring; then the other acetyl group, now with a lone pair of electrons, acts as a nucleophile to fuse the ring together as a five carbon ring, producing HFCA.

HFCA methyl ester is produced from HFCA by esterification of carboxylic acid with methanol. Dehydration at the carboxylic carbon of HFCA under acidic conditions produces a carbo-cation transition state, allowing for nucleophilic attack by methanol.

Chlorflurenol (CHF) is produced from HFCA when it is dissolved in methanol and reacted with chlorine gas at around 100° C.

Figure 1:
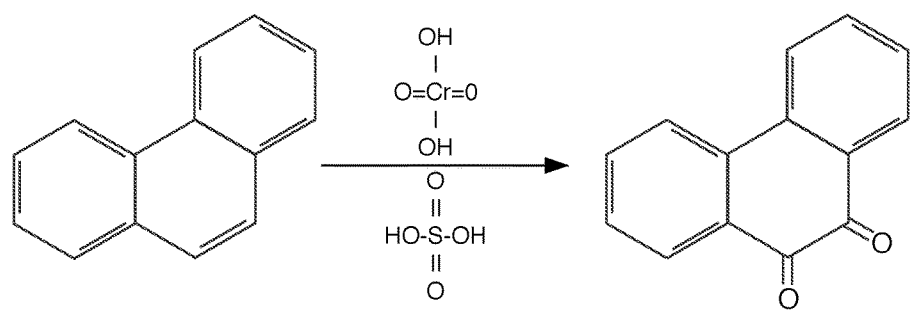
FIG. 1 is a diagram of the reaction of phenanthrene with chromic acid and sulfuric acid to form phenanthrenequinone.

Reaction of Phenanthrene into Phenanthrenequinone (FIG. 1)

While stirring, water, phenanthrene, sodium dichromate, and then the catalyst: tetraburyl ammonium fluoride-trihydrate (TBAF) were combined. Stirring continued and the mixture was headed to 95-100° C., then cooled to, and held at, 80-85° C. Sulfuric acid was slowly added by drops. For 6-8 hours a temperature of 80° C. was maintained and then the mixture was cooled to 50-55° C. Water was added slowly and the mixture was stiffed for 30 minutes. The mixture was centrifuged to separate the solid cake. The cake was washed with water and brought to pH 7. While stirring, water, sodium carbonate and the separated cake were combined and heated to 40-50° C. These conditions were held for one hour then the reaction product was centrifuged and washed thoroughly and brought to pH 7-7.5. The wet cake was dried for 13 hours to yield solid phenanthraquinone, m.p. 209-212° C.

In another experiment 200 lbs. phenanthrene (86%) is mixed with 561.8 lbs. Na$_2$Cr$_2$O$_7$.2H$_2$O and 448.5 g water. The mixture is reacted with 0.112 lbs. tetraethylammonium-fluoroctane sulfonate (a surfactant), heated up to 100° C. with agitation (180 rpm), and then cooled down to 80° C. While continuing agitation, 950 g of concentrated sulfuric acid is added within two hours and the temperature of the reaction mixture is maintained between 80 to 85° C. Agitation is continued for an hour at 85° C. and then the mixture is cooled down to 50° C. The precipitated phenanthrenequinone is isolated from the mixture and washed with water until the pH reaches 7. After drying, 197.19 lb. of phenanthrenequinone, m.p. 209° C. is obtained.

Figure 2:
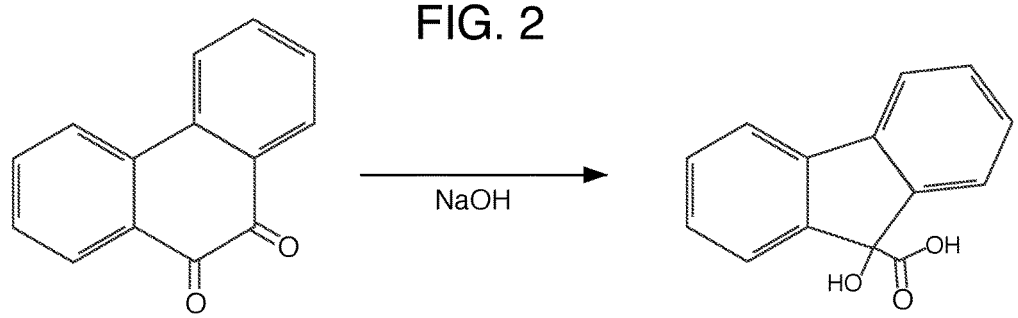
FIG. 2 is a diagram of the reaction of phenanthrenequinone with sodium hydroxide to form-9-hydroxyfluorene-9-carboxylic acid.

Reaction of Phenanthrenequinone into HFCA (FIG. 2)

While stirring water, NaOH and phenanthrenequinone were combined and then heated to 90-92° C., then cooled to room temperature. The mixture is centrifuged, the filtrate was collected and the cake was washed thoroughly using 25 L of distilled water. The filtrate and wash were combined, brought to pH 3-4 with HCl, centrifuged, and the mother liquor was collected. Dilute sulfuric acid is added to the mixture or the solution is diluted with sulfuric acid to pH 1-2. The material is centrifuged once more and the cake is collected. The cake was washed with more distilled water and dried to yield solid HFCA, m.p. 164-166° C. (54.1%).

Figure 3:
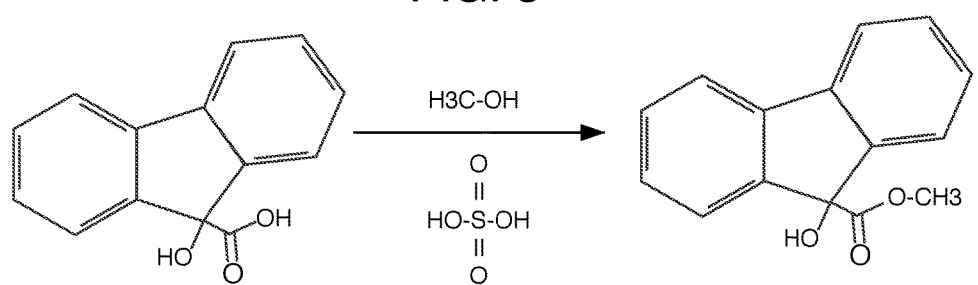
FIG. 3 is a diagram of the reaction of 9-hydroxy-fluorene-9-carboxylic acid methanol and sulfuric acid to form 9-hydroxy-fluorene-9-carboxylic acid-methyl ester.

Reaction of HFCA into HFCA-Methyl Ester (FIG. 3)

50.4 grams of HFCA is dissolved in 500 mL of methanol by mixing. To this, a concentrated solution of 5 mL sulfuric acid (0.089 mole) is added and the mixture is heated and allowed to reflux for an hour. After cooling to room temperature, 100 mL of liquid sodium bicarbonate is added until the mixture reached a pH of about 8. Most of the methanol is evaporated using a rotary evaporator, and the aqueous solution is removed via a dichloromethane-water liquid layer extraction. The combined organic layers are dried over anhydrous magnesium sulfate and the solvent is distilled off. HFCA-methyl ester is purified by recrystallization from diethyl ether to yield about 11.4 grams as a white crystalline material. It has a melting point of around 158-163° C. (21.3%)

Figure 4:
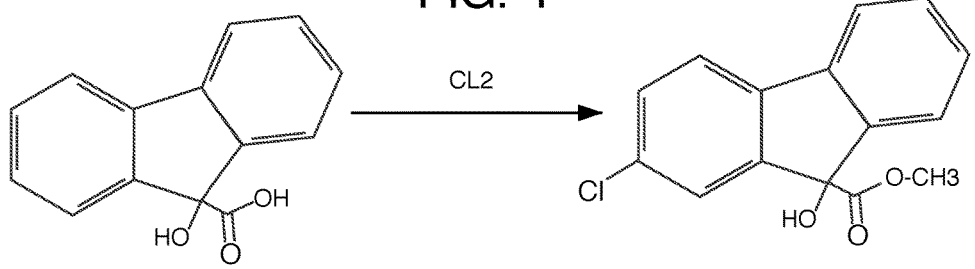
FIG. 4 is a diagram of the reaction of 9-hydroxy-fluorene-9-carboxylic acid with chlorine to form chlorflurenol.

Reaction of HFCA to Chlorflurenol (FIG. 4)

To make chlorflurenol, HFCA is dissolved in methanol and reacted with chlorine gas in order to convert into chlorflurenol-methyl ester. In this process, HFCA is converted into a mixture of HFCA-methyl ester, 2-chlorohydroxyflurene-methyl ester and 2,7-dichlorohydroxyfluorene-methyl-ester. Depending on the conditions used during chlorination, 2-chlorohydroxyfluorene-methyl-ester is predominantly formed (more than 70% of the mixture). The unreacted HFCA-methyl-ester is formed up to 20% and dichloro-hydroxyfluorene-methyl ester is about 10%. This product is called chlorflurenol-methyl ester (CFM) which is registered for use as a plant growth regulator and has a melting point of 136-142° C.

I claim:

1. A method for producing a chemical from phenanthrene comprising the steps of
   a. combining phenanthrene, sodium dichromate and tetrabutyl ammonium fluoride-trihydrate while stirring,
   b. heating the mixture to 95-100° C.,
   c. cooling the mixture to 80-85° C.,
   d. slowly adding sulfuric acid,
   e. allowing the reaction to proceed at 80-85° C. for 6-8 hours,
   f. cooling the reaction mixture to 50-55° C.,
   g. adding water,
   h. collecting the precipitate with the aid of a centrifuge,
   i. washing the precipitate,
   j. neutralizing the pH of the precipitate;
   k. drying the precipitate;
   l. reacting the precipitate with an alkaline species to yield HFCA (9-hydroxyfluorene-9-carboxylic acid).

2. The method of claim 1 in which the alkaline species is sodium hydroxide.

3. The method of claim 1 further comprising the step of reacting the final product of claim 1 with methanol, sulfuric acid, and sodium bicarbonate to yield HFCA methyl ester.

4. The method of claim 1 further comprising the step of reacting the final product of claim 1 with butanol to yield flurenol butyl ester.

5. The method of claim 1 further comprising the step of dissolving the final product of claim 1 in methanol and reacting it with chlorine gas to yield chlorflurenol.

* * * * *